United States Patent [19]

Freedman et al.

[11] Patent Number: 5,407,954
[45] Date of Patent: Apr. 18, 1995

[54] ARYLALKOXYPHENOXY-IMIDAZOLINE COMPOUNDS

[75] Inventors: Jules Freedman; Bruce M. Baron, both of Cincinnati; Mark W. Dudley, Somerville, all of Ohio

[73] Assignee: Merrell Dow Pharmaceuticals Inc., Cincinnati, Ohio

[21] Appl. No.: 194,137

[22] Filed: Feb. 9, 1994

Related U.S. Application Data

[63] Continuation of Ser. No. 990,174, Dec. 24, 1992, abandoned, which is a continuation-in-part of Ser. No. 832,556, Feb. 6, 1992, Pat. No. 5,216,008.

[51] Int. Cl.$^6$ .................. A61K 31/415; C07D 233/22
[52] U.S. Cl. .................. 514/401; 548/349.1; 548/353.1
[58] Field of Search .............. 514/401; 548/349.1, 548/353.1

[56] References Cited

FOREIGN PATENT DOCUMENTS 0423802  4/1991  European Pat. Off. .

OTHER PUBLICATIONS

Hartig, et al., The 5-HT$_{1c}$ Receptor, Annals New York Acad. of Science, vol. 600, 149–167 (1990).
Armah, et al., Int. Symp. on Serotonin, Florence, Italy, Mar. 29–Apr. 1, 1989, Abstr. p. 40.
Hibert, M. F. et al., J. Med. Chem. 1988, 31, 1087–1093.
Schoeffter, P. et al., Eur. J. Pharmacol 1991, 196, 213–216.
Middlemiss, D. N., Eur. J. Pharmacol 1984, 101,289–293.
Pierson, M. E. et al., J. Med. Chem. 1989, 32, 859–863.
Nikam, S. S. et al., J. Med. Chem. 1988, 31, 1965–1968.
Chapleo, et al. J. Med. Chem. 26:823–831 (1983).
Hartig, et al., Annals New York Acad. of Sci., vol. 600, 149–167 (1990).
Melloni, et al., Eur. J. Med. Chem. 26:207–213 (1991).
Canton, et al., Eur. J. of Pharmacology 191:93–96 (1990).
van der Heyden, et al., Physchopharmacology 101 Supp., S58 (1990).
Yagaloff, et al., Brain Research, 385: 389–394 (1986).
Curzon, et al., TIPS 11:181–2 (1990).
Glover, et al., TIPS, vol. 10(1):1–3, Jan. 1989.
Fozard, et al., TIPS, vol. 10:307–308, Aug. 1989.

*Primary Examiner*—Patricia L. Morris
*Attorney, Agent, or Firm*—Kenneth J. Collier

[57] ABSTRACT

The present invention is directed to a new class of arylalkoxyphenoxy-imidazoline compounds and their use for the treatment of depression, anxiety, hypertension, and migraine headaches.

26 Claims, No Drawings

ARYLALKOXYPHENOXY-IMIDAZOLINE COMPOUNDS

CROSS-REFERENCE TO RELATED APPLICATION

This is a continuation of application Ser. No. 07/990,174, filed Dec. 24, 1992, now abandoned; which is a continuation-in-part of application Ser. No. 07/832,556, filed Feb. 6, 1992, now U.S. Pat. No. 5,216,008.

The present invention is directed to a new class of arylalkoxyphenoxy-imidazoline compounds possessing therapeutic properties. Therein, another aspect of the invention is directed to a method of use of these compounds for the treatment of depression, anxiety, hypertension, and migraine headaches. A further aspect of the invention is directed to pharmaceutical compositions containing these arylalkoxyphenoxy-imidazoline compounds.

In accordance with the present invention, a new class of arylalkoxyphenoxy-imidazoline compounds have been discovered which can be described by the following formula (Formula 1):

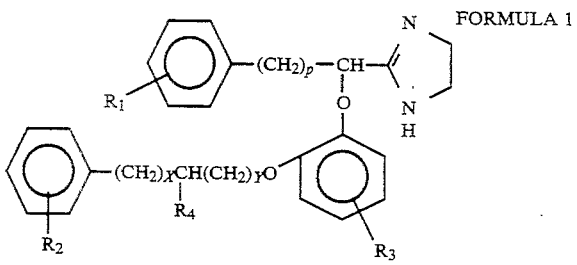

FORMULA 1 wherein;

R₁ is represented by a substituent selected from the group consisting of hydrogen, halogen, $C_{1-4}$ alkyl, $C_{1-4}$ alkoxy, $-NO_2$ and $-NR_5R_6$;

R₂ is represented by a substituent selected from the group consisting of hydrogen, halogen, $C_{1-4}$ alkyl, $C_{1-4}$ alkoxy, $-NO_2$ and $-NR_5R_6$;;

R₃ is represented by a substituent selected from the group consisting of hydrogen, halogen, $C_{1-4}$ alkyl, and $C_{1-4}$ alkoxy;

R₄ is represented by a substituent selected from the group consisting of hydrogen, halogen;

R5 and R6 is independently selected from hydrogen and $C_{1-4}$ alkyl;

p is represented by the integer 0, 1, 2, 3, or 4;

x is represented by an integer from 0-2;

y is represented by an integer from 0-2;

with the proviso that at least $R_1$ or $R_2$ is chosen as $NO_2$ or $-NR_5R_6$. Further, compounds of this invention can also be represented by the pharmaceutically compositions or acceptable addition salts thereof. It is further understood that any one or more preferred groups may exist together in combinations forming a more preferred grouping of the claimed compounds.

Preferred groups of the claimed compounds, but not limited to, are such that

R₁ is represented by hydrogen, $C_{1-4}$ alkoxy, $-NO_2$, or $NR_5R_6$;

R₂ is represented by hydrogen, $-NO_2$, or $-NR_5R_6$;

R₃ is represented by hydrogen;

R₄ is represented by hydrogen;

R5 and R6 is independently selected from hydrogen and a $C_{1-4}$ alkyl;

p is represented by an integer 1, 2, or 3;

x is represented by an integer from 0-2;

y is represented by an integer from 0-2;

with the proviso that at least $R_1$ or $R_2$ is chosen as $NO_2$ or $-NR_5R_6$; and compounds of this invention can be represented by the pharmaceutically acceptable addition salts thereof. It is further understood that any one or more the especially preferred groups may exist together in combinations forming a more preferred subgrouping of the preferred compounds.

As used in this application:

a) the term "halogen" refers to a fluorine, chlorine, or bromine atom;

b) the terms "lower alkyl group and $C_{1-4}$ alkyl" refer to a branched or straight chained alkyl group containing from 1–4 carbon atoms, such as methyl, ethyl, n-propyl, isopropyl, n-butyl, isobutyl, etc.;

c) the terms "lower alkoxy group and $C_{1-4}$ alkoxy" refer to a straight or branched alkoxy group containing from 1–4 carbon atoms, such as methoxy, ethoxy, n-propoxy, isopropoxy, n-butoxy, isobutoxy, etc.;

d) the term "pharmaceutically acceptable addition salt refers to either a basic addition salt or an acid addition salt.

e) the term "$-NR_5R_6$" refers to either a substituent amino group where in R5 and R6 may independently be a hydrogen or a $C_1-C_4$ alkyl group.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids Such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal hydroxides such as sodium or potassium.

All of the compounds of Formula I contain at least one asymmetric center and therefore exist as enantiomers. Any reference in this application to one of the compounds represented by Formula I is meant to encompass either a specific enantiomer or a mixture of enantiomers. The specific enantiomers can be separated and recovered by techniques known in the art such as chromatography on chiral stationary phases or resolution via chiral salt formation and subsequent separation by selective crystallization.

The compounds of Formula I show three phenyl rings optionally substituted. These rings may be optionally substituted as indicated by the definition for their respective R groups.

When $R_1$ is other than a hydrogen atom, there can be up to 3 monovalent substituents occurring on the indicated phenyl ring. These substituents can be the same or different and can be located at any of the ortho, meta, or para positions When $R_1$ or $R_2$ is chosen to be amino as represented by the formula $-NR_5R_6$, $R_5$ and $R_6$ are chosen independently from hydrogen or a $C_1-C_4$ alkyl group. A preferred grouping would elect $R_5$ and $R_6$ to both be hydrogen or to both be a $C_1-C_4$ alkyl group.

When $R_3$ is other than a hydrogen atom, there can be up to 4 monovalent substituents bonded to this phenyl ring. These substituents may be located at any of positions 3, 4, 5, or 6. These substituents may be the same or different. This divalent substituent will form bicyclic ring systems similar to those depicted above except that the divalent substituent may be bonded! to positions 3 and 4, positions 4 and 5, or positions 5 and 6. Only one divalent substituent may be bonded to this phenyl ring.

$R_4$ bonds to a methylene carbon atom. $R_4$ can be selected from the group consisting of hydrogen and $C_{1-4}$ alkyl.

Illustrative compounds encompassed by Formula I include:
a)   2-(1-[2-(2-phenylethoxy)phenoxy]-2-phenyl)ethylimidazoline
b)   2-[1-(2-benzyloxyphenoxy)-4-phenyl]butylimidazoline
c)   2-[1-(2-benzyloxyphenoxy)-2-(4-methoxyphenyl)ethylimidazoline
d)   2-[1-[2-benzyloxyphenoxy)-2-phenyl]ethylimidazoline
e)   2-(1-[2-(4-chlorobenzyloxy)phenoxy]-2-phenyl)ethylimidazoline
f)   2-(1-[4-methoxybenzyloxy)phenoxy]-2-phenyl)ethylimidazoline
g) 2-[α-(2-benzyloxyphenoy)]benzylimidazoline
h)   2-(1-[2-(1-phenylethoxy)phenoxy]-2-phenyl)ethylimidazoline
i)   2-(1-[2-(3-fluorobenzyloxy)phenoxy]-3-phenyl)propylimidazoline
j)   2-[1-(2-benzyloxy-4-fluorophenoxy)-2-(3-methoxyphenyl]ethylimidazoline
k)   2-[1-(2-benzyloxy-6-methoxyphenoxy)-3-phenyl]propylimidazoline
2-([2-(3,4-diclorobenzyloxy)phenoxy]-3-phenyl)propylimidazoline Further illustrative compounds encompassed by Formula I include
m)   2-(1-[2-(4-aminobenzyloxy)phenoxy]-2-phenyl)ethylimidazoline;
n)   2-(1-[2-(4-nitrobenzyloxy)phenoxy]-2-phenyl)ethylimidazoline;
n)   2-(1-[2-(4-aminobenzyloxy)phenoxy]-2-phenyl)propylimidazoline;
o)   2-(1-[2-(4-nitrobenzyloxy)phenoxy]-2-phenyl)propylimidazoline;
p)   2-(1-[2-(4-aminobenzyloxy)phenoxy]-2-phenyl)butylimidazoline;
q)   2-(1-[2-(4-nitrobenzyloxy)phenoxy]-2-phenyl)butylimidazoline;
q)   2-[1-(2-benzyloxyphenoxy)-2-(4-nitrophenyl)ethylimidazoline;
r)   2-[1-(2-benzyloxyphenoxy)-2-(4-aminophenyl)ethylimidazoline;
q)   2-[1-(2-benzyloxyphenoxy)-2-(4-nitrophenyl)-propylimidazoline;
r)   2-[1-(2-benzyloxyphenoxy)-2-(4-aminophenyl)-propylimidazoline;
q)   2-[1-(2-benzyloxyphenoxy)-2-(4-nitrophenyl)-butylimidazoline;
r)   2-[1-(2-benzyloxyphenoxy)-2-(4-aminophenyl)-butylimidazoline;

SYNTHETIC METHODS

The compounds of Formula I can be synthesized using techniques that are known, in the art. One method for synthesizing these compounds is disclosed in Reaction Scheme I.

REACTION SCHEME I
STEP A

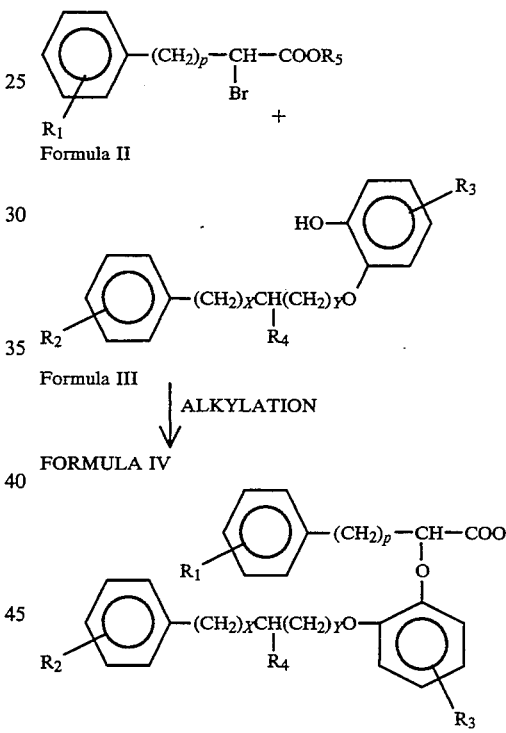

The first step in the reaction sequence to produce compounds of formula 1 is to conduct an alkylation reaction between a bromo ester of Formula II and the substituted phenol of Formula III. The appropriate starting materials area bromo ester of formula II and the phenol of formula II, in which p and $R_1$ and which $R_2$, $R_3$, $R_4$, X and Y, have the same definitions as that appearing in the final product. The particular $C_{1-4}$ alkyl which is present at the $R_5$ position does not effect the final structure, since this substituent will not be retained in the final product.

The alkylation reaction can be conducted utilizing techniques well known in the art. Approximately equimolar amounts of the bromo ester of Formula II and the phenol of Formula III are contacted in an organic solvent such as acetone or acetonitrile. The reactants are typically contacted in the presence of a base such as $K_2CO_3$. This base is typically present in excess. The reactants are then heated to reflux and the reaction is allowed to proceed for a period of time ranging from about 10 to 96 hours.

The resulting oxy ester intermediate of Formula IV can be recovered from the reaction medium and purified using techniques known in the art. The oxy ester intermediate is typically recovered by concentration as is known in the art. This oxy ester intermediate can then be purified by either distillation or by recrystallization from a solvent such as pentane or hexane using techniques known in the art.

As depicted below in Step B of Reaction Scheme I, the next step in the synthesis is to conduct an amidation reaction between the oxy ester intermediate of Formula IV and ethylenediamine as described by Formula V, in which $R_1$, $R_2$, $R_3$, $R_4$, p, X and Y are as as above. The product of this amidation reaction then cyclizes in-situ thereby producing the desired compound of Formula I. Amidation and cyclization serves to place the imidazoline moiety on the oxy ester intermediate of Formula IV, thereby producing the desired compound of Formula I.

This amidation reaction can be conducted using techniques well known in the art. Approximately equimolar amounts of the oxy ester intermediate and the ethylenediamine are contacted in an organic solvent such as toluene. A suitable organo-metallating agent, such as $Al(CH_3)_3$, is added to the reaction mixture and the reactants are heated to reflux for a period of time ranging from about 3 to 8 hours. Typically from 1 to about 1.5 equivalents of the organo-metallating agent is utilized. The product of the amidation reaction will cyclize in-situ during this refluxing period, thereby producing the desired compound of formula I.

The resulting compound of Formula I can be recovered and purified by techniques known in the art. For example, the compounds can be recovered from the reaction zone by either concentration or extraction. The compounds of Formula I can then be purified by chromatographic techniques known in the art such as silica gel chromatography Alternatively, they can also be purified by recrystallization from a solvent system such as hexane or cyclohexane.

Methods for obtaining or producing the phenols of Formula III, and the bromo esters of Formula II, are known in the art.

Alternatively the oxy intermediates of Formula IV can be prepared as disclosed below in Reaction Scheme II:

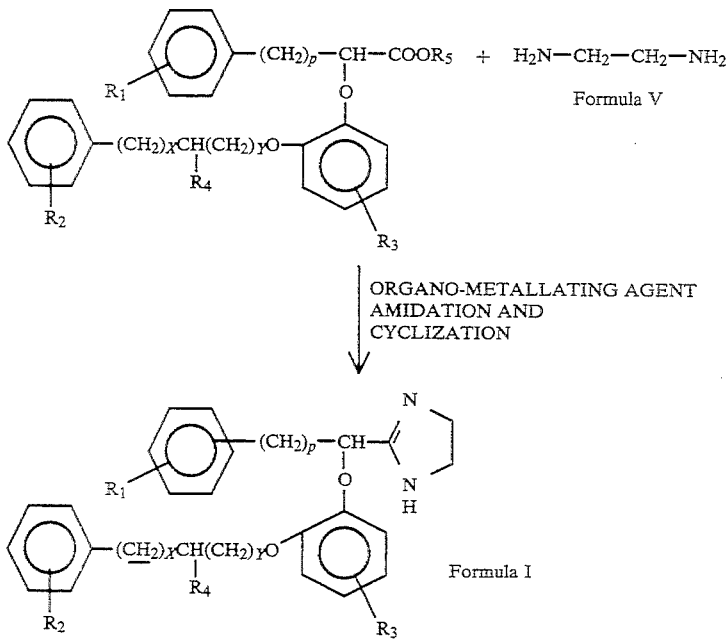

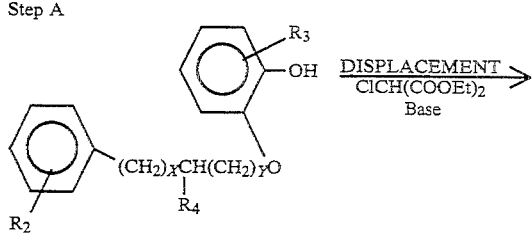

REACTION SCHEME II -continued
STEP B

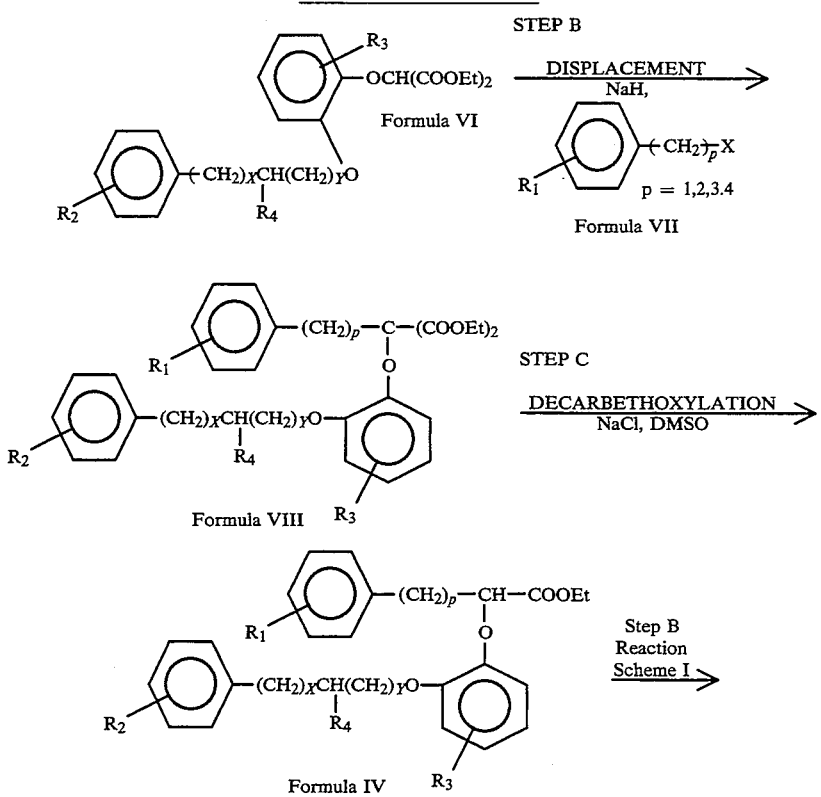

As is depicted in Reaction Scheme II, the initial step (Step A) is to carry out a displacement reaction between a substituted phenol as previously described by Formula III in which $R_2$, $R_3$, $R_4$, X and Y are as defined above and diethyl chloromalonate. This produces the phenoxy derivative of Formula VI in which $R_2$, $R_3$, X and Y are as in Formula I.

In Step B the phenoxy derivative is subjected to a displacement reaction with a haloalkylphenyl derivative as shown by Formula VII, in which $R_1$ and p are as in Formula I and X represents a halogen, to produces the intermediate of Formula VIII. The formula VIII intermediate is then subjected to a decarbethoxylation reaction to produce the oxy ester of Formula IV in which $R_5$ is an ethyl moiety as depicted. The desired compound of Formula I can then be produced by the amidation and cyclization reaction depicted in Step B of Reaction Scheme I.

The proper starting material to utilize in the displacement reaction of Step A of Reaction Scheme II is a phenol derivative in which $R_2$, $R_3$, $R_4$, X and Y, are represented by the same substituents as is desired in the final product of Formula I. The displacement reaction of Step A can be carried out using techniques known in the art. Typically approximately equivalent amounts of the phenol derivative and the diethyl chloromalonate are contacted in the presence of an excess of a base such as potassium carbonate. The reactants are heated to reflux in an organic solvent such as acetone for a period of time ranging from 10 to 48 hours. The desired phenoxy derivatives of Formula VI can be recovered by filtration and purified by distillation as is known in the art.

The displacement reaction of Step B is typically carried out in the following manner. The phenoxy derivative of Formula VI is contacted with 1.1 equivalents of sodium hydride in excess dimethylformamide at a temperature range of from 5° to 10° C. for a period of time from 0.5 to 1 hour. An equivalent amount of the haloalkylphenyl derivative of Formula VII, having p equal to 1, 2, 3, or 4, is then added to the reaction and the reactants are heated to a temperature range of from 55° to 60° C. for a period of time from 2 to 6 hours. The desired intermediates of Formula VIII can be recovered by extraction and purified by distillation as is known in the art.

The decarbethoxylation of Step C is carried out by contacting the intermediate of Formula VIII with approximately 2 equivalents of water, 1 equivalent of NaCl, and an excess of DMSO. The reactants are heated to reflux under a nitrogen atmosphere for a period of time ranging from 2 to 8 hours. The desired oxy ester of Formula IV can be recovered by extraction and purified by distillation as is known in the art.

Alternatively the oxy intermediates of Formula IV can be prepared as disclosed below in Reaction Scheme III.

REACTION SCHEME III

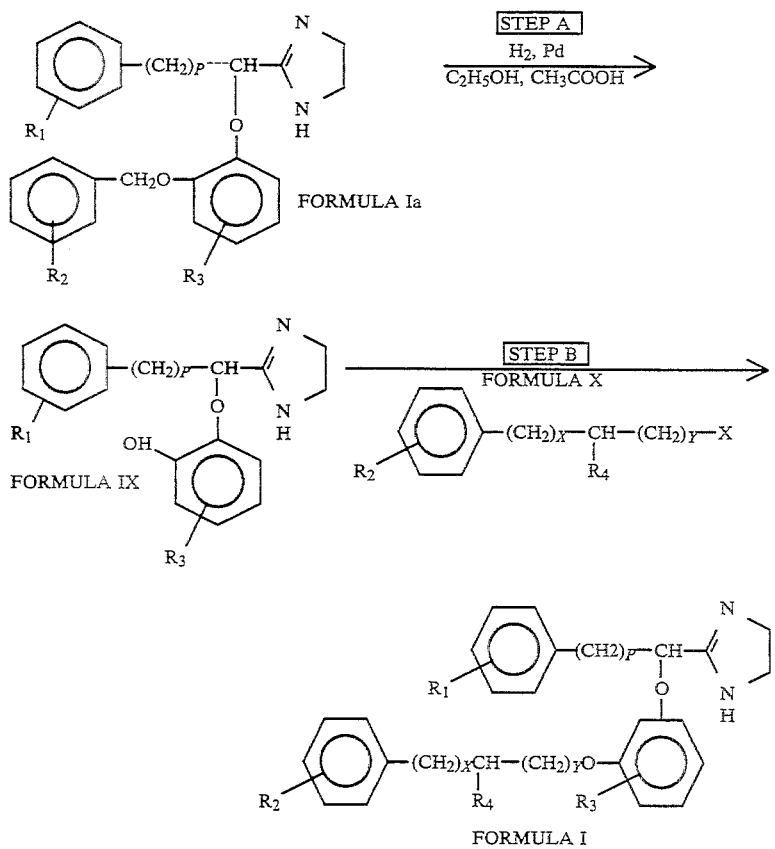

Compounds of Formula Ia shown in Reaction Scheme III, are able to be converted to different compounds of formula I. It is understood that compounds of formula Ia are compounds of formula I wherein $R_4$ is hydrogen, X and Y are zero, and the other substituents are the same definitions as the desired product (herein referred to as Formula Ia).

Reaction Scheme III depicts a two step reaction to form compounds of formula I. As depicted in Reaction Scheme III, Step A, compounds of formula Ia are hydrogenated to form compounds of formula IX, in which $R_1$, $R_2$, $R_3$, p, and m are the same definitions as appear in the final product. The hydrogenation of Step. A is typically performed by placing Ia compounds in a ethanol/acetic acid solution. Catalyst is then added and hydrogenation in a hydrogen atmosphere under pressure is carried out with agitation for 1–8 hours as is known in the art. Typically the catalyst is a palladium derivative. The hydrogenated product is recovered by evaporation Of the solvent and redissolving the oil in acetone or other suitable solvent containing sightly more than one equivalent of hydrochloric acid. The final product may then be recovered by precipitation and or recrystallization to recover the final product of formula IX or its salt.

Compounds of formula IX or their salts can then be used to produce compounds of formula I by reacting the formula IX compound with those compounds of formula X shown in Step B of Reaction Scheme III. Typically, the hydrochloride salt of formula IX is reacted in a solution of methanol containing two equivalents of sodium methoxide to which the haloalkylphenyl derivative of formula X is added, and refluxed for several hours. After filtration, the solvent can be removed and the product isolated by chromatography on silica gel. Final recrystallization or precipitation results in the final product of formula I.

Compounds of formula I having nitro (—$NO_2$) group as a substituent of $R_1$ or $R_2$ are synthesized by selecting precursors of formulas III, IV, and VI, found in Reaction Schemes I and II, having a nitro containing functionality. In addition, precursors of formula X (Reaction Scheme III) can be used to incorporate nitro groups into the $R_2$ position.

Compounds of formula X, wherein $R_1$ or $R_2$ are defined as containing a nitro group (—$NO_2$), may be reduced to form the corresponding amino group (—$NH_2$) of formula XI. Reduction may be accomplished by use of a number of commonly known methods of reduction, i.e., palladium-carbon and hydrogen gas, stanous chloride or iron chloride with hydrochloric acid, and the like, to produce the desired amino functionality (Step A in Scheme IV).

Optionally the compounds of Formula XI may be further reacted further with a $C_1$–$C_4$ aldehyde (RCHO) to alkylate the substituent amino group, Which optionally may be reduced with sodium borohydride, or the like, to produce the disubstituted $C_1$–$C_4$ alkyl derivative. Compounds having monosubstituted alkyl groups may be synthesized by either selective reaction or selective protection of the amino functionality as would be known to one skilled in the art.

GENERAL BIOLOGY

The compounds of Formula I exhibit multiple pharmacological properties. The compounds of Formula I are useful in that they bind the 5-HT$_{1C}$ receptor. The compounds are

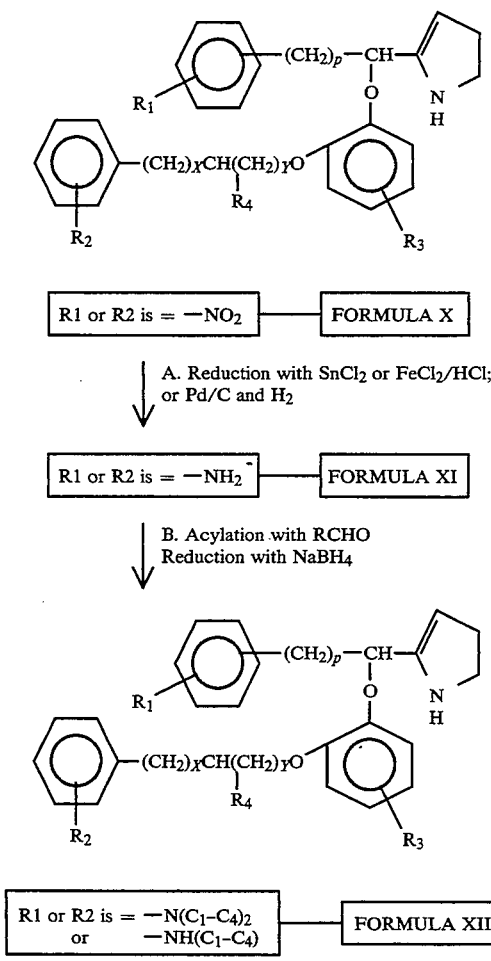

REACTION SCHEME IV also useful in that they have affinity for the 5-HT$_2$ receptor and may have appreciable affinities for the α-2 receptor. Due to these pharmacological properties, the compounds are useful as in the treatment of depression, anxiety, hypertension, and migraine headaches.

The 5HT$_{1c}$ receptor is one class of serotonin receptors. It was discovered by two independent investigations: Pazors et al. (Eur. J. Pharmacol., 106,539-546 (1984); Eur. J. Pharmacol. 105:531-538(1984)) discovered this receptor in porcine choroid plexus by the use of [$^3$H]mesulergine while Yagaloff, et al. (J. Neurosci. 5,3178-3183 (1985)) found the receptors present in rat choroid plexus with [$^{125}$I]LSD. Both rat and pig choroid plexus have provided model systems for study of the 5HT$_{1c}$ receptor. Recombinant technologies have also lead to recombinant cell lines having the 5HT$_{1c}$ receptor.

In addition to quantifying the location of 5-HT$_{1c}$ receptor protein by ligand binding assays, the location of 5HT$_{1c}$ receptor mRNA can be identified and quantified by RNA blot analysis. In situ hybridization histochemistry also provides another technique which provides cellular resolution and sensitivity for assaying the 5HT$_{1C}$ receptor.

Use of these tools have led to the observation that the regional distribution of 5HT$_{1c}$ receptors in the limibic system may affect mood, behavior and hallucinogenesis while hypothalamic 5HT$_{1c}$ receptors may influence sleep, appetite thermoregulation, sexual behavior and neuroendocrine function.

It has been reported that the 5HT$_{1c}$ receptor may be a key factor in the activation of migraines. TIPS (Aug)10, 307-9 (1989). This observation is based on the fact that m-chlorophenylpiperazine (m-CCP), a known 5-HT$_{1C}$ receptor agonist, was observed to be capable of inducing migraine headaches. Breweton, et al., Clin. Pharmacol. Ther. 43, 605-609 (1988). Further work by Hoyer and his colleagues by using in vitro radioligand binding and second messenger responses have demonstrated that m-CPP also has properties as a 5-HT$_{1C}$ and a 5-HT$_{1b}$ receptor agonist. Since the 5-HT$_{1b}$ sites appear to be rodent specific it is likely that m-CCP acts rather selectively at 5-HT$_{1C}$ receptor in humans. Since compounds of the present invention operate as 5HT$_{1C}$ receptor antagonists they may be useful in the prevention or alleviation of migraines, depression, or anxiety occurring through the 5-HT$_{1C}$ receptor.

It has been reported that 5HT$_{1C}$ antagonists may be an effective means in humans for treatment of the symptoms of migraines. Both methysergide and pizotifen have been shown to have potent 5-HT$_{1C}$ receptor antagonist activities (albeit nonselective). Fozard, J. R. (1988) in The Management of Headache (Clifford Rose, F., ed.), pp. 97-114. Further, both methylsergide and pizotifen are well established as effective migraine prophylactic agents. Similarly, cyproheptadine and mianserin have been suggested to be working through the 5-HT$_{1C}$ receptor in the treatment of migraines (Peatfield, R. (1986) Headache, Springer; Monro, P., Swade, C. and Coppen (1985 ) Acta Psychiatr. Scand. 72 ( Suppl. 320 ), 98-103 Since the compounds of the instant invention are 5HT$_{1C}$ antagonists, they potentially are useful in the treatment of migraines and the symptoms of migraines.

As used in this application, the term "migraine" should be construed as encompassing those conditions, but not limited to, which the medical profession have referred to as a paroxysmal disorder characterized by recurrent attacks of headache, with or without associated visual and GI disturbances. (Merck Manual, 15th Edition, (Merck Sharp & Dohme Research Laboratories, R. Berkow, Editor) 1355-1366 (1987). Further descriptions of the symptoms include possible associated nausea, photophobia, throbbing, unilaterally and involuntary vomiting.

In order to exhibit an anti-migraine effect, it is necessary that the compounds be administered to the patient in an effective amount. The dosage range at which these compounds exhibit this migraine prophylactic effect can vary widely depending upon the severity of the patient's depression, the particular compound being administered, the route of administration, the co-administration of other therapeutic agents, and the presence of other underlying disease states. Typically, the compounds will be administered at a dosage range of from 0.1 mg/kg/day to about 100 mg/kg/day. Repetitive daily administration may be desirable and will vary with the conditions described above. However, the compounds are typically administered from 1 to 4 times daily.

The affinity of the compounds for the 5HT$_{1C}$ receptor can be demonstrated by receptor binding assay procedures which are known in the art. The affinity of compounds for the 5HT$_{1C}$ receptor has also been demonstrated by receptor binding assay procedures which are disclosed by Hartig et al. *Ann N.Y. Acad. Sci* 600, 149 (1990) and Canton, et al. *Eur. J. Pharm.* 191, 93–96 (1990).

Binding of the natural ligand to the 5HT$_{1C}$ receptor leads to the production of second messengers, such as phosphatidylinositol and diacylglycerol. Use of assays for second messengers can be used to characterize the agonistic or antagonistic properties of agents that bind the 5HT$_{1C}$ receptor. Furthermore, such assays when coupled with the knowledge of the target cell type can lead one to claim their potential role as therapeutic agents.

In order to exhibit an anti-depressant effect, it is necessary that the compounds be administered to the patient in an effective amount. The dosage range at which these compounds exhibit this anti-depressant effect can vary widely depending upon the severity of the patient's depression, the particular compound being administered, the route of administration, the co-administration of other therapeutic agents, and the presence of other underlying disease states. Typically, the compounds will be administered at a dosage range of from 0.1 mg/kg/day to about 100 mg/kg/day. Repetitive daily administration may be desirable and will vary with the conditions described above. However, the compounds are typically administered from 1 to 4 times daily.

As used in this application, the term "depression" should be construed as encompassing those conditions which the medical profession have referred to as major depression, endogenous depression, psychotic depression, involutional depression, involutional melancholia, etc. These conditions are used to describe a condition in which patients typically experience, but not limited to, intense sadness and despair, mental slowing, loss of concentration, pessimistic worry, despair, and agitation. The patients often experience physical complaints such as insomnia, anorexia, decreased energy, decreased libido, etc.

The compounds of Formula I will elevate the patient's mood if they are suffering from depression and either relieve or alleviate the physical complaints which the patient is experiencing.

The anxiolytic properties of these compounds can also be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C. R., Distress vocalization in rat pups: a simple screening method for anxiolytic drugs. *J. Pharmacol. Methods*, 14: 181–187 (1985) and Insel et al., Rat pup ultrasonic isolation calls: Possible mediation by the benzodiazepine receptor complex, *Pharmacol. Biochem. Behav.*, 24:1263–1267 (1986).

As used in this application, the term "anxiety" refers to the unpleasant emotional state consisting of, but not limited to, psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension.

In order to exhibit this anxiolytic effect, it is necessary that the compounds be administered to the patient in an effective amount. The dosage range at which these compounds exhibit this anxiolytic effect can vary widely depending upon the severity of the patient's anxiety, the particular compound being administered, the route of administration, the co-administration of other therapeutic agents, and the presence of other underlying disease states. Typically, the compounds will be administered at a dosage range of from about 0.1 mg/kg/day to about 100 mg/kg/day. Repetitive daily administration may be desirable and will vary with the conditions described above. However, the compounds are typically administered from 1 to 4 times daily.

The anti-hypertensive properties of the compounds can be demonstrated by animal models known in the art such as the spontaneously hypertensive rat. This protocol has been described by Dage et al., *Journal of Cardiovascular Pharmacology* 3: 299–315 (1981).

In order to exhibit an antihypertensive effect, it is necessary that the compounds be administered to the patient in an effective amount. The dosage range at which these compounds exhibit this effect can vary widely depending upon the severity of the patient's condition, the particular compound being administered, the route of administration, the co-administration of other therapeutic agents, and the presence of other underlying disease states. Typically, the compounds will be administered at a dosage range of from 0.01 mg/kg/day to about 100 mg/kg/day. Repetitive daily administration may be desirable and will vary with the conditions described above. However, the compounds are typically administered from 1 to 4 times daily.

The compounds of the present invention may be administered by a variety of routes. They are effective if administered orally. The compounds may also be administered parenterally (i.e. subcutaneously, intravenously, intramuscularly, or intraperitoneally).

Since the compounds of formula I act as serotonin 5HT$_2$ antagonist, they may be useful in the treatment of a variety of disease states and conditions related with the treatment of 5HT$_2$ antagonist; such as it may be useful in the treatment of anxiety, anorexia nervosa, hypertension, intermittent claudication, and Raynaud's phenomenon. These conditions and diseases can be relieved by administering to a patient in need thereof of Compounds of formula in an amount sufficient to treat the disease or condition (i.e. an anxiolytic amount, a anti-anorexic amount, etc.). This quantity will be within the dosage range at which the compound exhibits its serotonin 5HT$_2$ antagonistic properties. Ketanserin is a prototype of a 5-HT2 antagonist. Ketanserin blocks the receptor responsible for 5-HT$_2$-induced action.

The dosage range at which compounds of formula could exhibits its ability to block the effects of serotonin at the 5HT$_2$ receptor can vary depending upon the particular disease or condition being treated and its severity, the patient, other underlying disease states the patient is suffering from, and other medications that may be concurrently administered to the patient. Generally though, this compound will exhibit its serotonin 5HT$_2$ antagonist properties at a dosage range of from about 0.001 mg/kg of patient body weight/day to about 100.0 mg/kg of patient body weight/day. The compound is typically administered from 1–4 times daily. Alternatively, it can be administered by continuous infusion. The compounds can be administered orally or parenterally to achieve these effects.

Affinity of the formula I compounds for the $5HT_2$ receptor can be demonstrated by receptor binding assays. Competition receptor binding assays for the $5HT_2$ receptor known in the art. These include testing for affinity for $5HT_2$ receptors on (1) transfected fibroblast cell membranes with [$^{125}$I]lysergic acid diethylamide, (2) cerebrocortical tissues using [$^3$H] spiroperidol, and (3) brain tissues using [$^3$H]mianserin.

Several tests have been developed for testing the effectiveness of $5HT_2$ antagonists in vivo. The administration of 5-methoxy-N,N-dimethyltryptamine (5-MeO-DMT) to mice typically produces a characteristic head twitch in the mice. In this test, the mice are administered 5-MeO-DMT and a test compound. An absence of head twitches in the mice is considered to be predictive of the ability of the test compound to antagonize the $5HT_2$ receptor in vivo.

As used in this application the terms anxiety, depression, hypertension, migraine and like diseases herein mention associated with treatment of $5HT_2$ and $5HT_{1C}$ antagonists are used in the manner defined in the 27th Edition of Dorland's Illustrated Medical Dictionary.

As used in this application:
a) the term "patient" refers to warm blooded animals such as, for example, guinea pigs, mice, rats, cats, rabbits, dogs, monkeys, chimpanzees, and humans;
b) the term "treat" refers to the ability of the compounds to either relieve, alleviate, or slow the progression of the patient's disease.

Pharmaceutical compositions can be manufactured utilizing techniques known in the art. Typically an antidepressant or anxiolytic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or,gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered As either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

The compounds of Formula I may also be admixed with any inert carrier and utilized in laboratory assays in order to determine the concentration of the compounds within the serum, urine, etc., of the patient as is known in the art.

EXEMPLARY COMPOUNDS OF FORMULA I AND PHYSICAL CHARACTERISTIC a) 2-(1-[2-phenylethoxy)phenoxy]-2-phenyl)ethylimidazoline mp. 102°−103°; Anal., Calcd. for $C_{25}H_{26}N_2O_2$: Theoretical %: C=77.69; H=6.78; N=7.25 Found %: C=77.55; H=6.75; N=7.16.

b) 2-[1-(2-benzyloxyphenoxy)-4-phenyl]-butylimidazolinem.

p. 80°−84°; Anal., Calcd. for $C_{26}H_{28}N_2O_2$: Theoretical %: C=77.97; H=7.05; N=7.00 Found % C=78.09; H=6.95; N=6.77.

c) 2-[1-(2-benzyloxyphenoxy)-2-(4-methoxyphenyl)]ethylimidazoline m.p. 122°−125°; Anal., Calcd. for $C_{25}H_{26}N_2O_3$: Theoretical %: C=74.60; H=6.51; N=6.96 Found %: C=74.35; H=6.57; N=6.67.

d) 2-[1-(2-benzyloxyphenoxy)-2-phenyl]ethylimidazoline m.p. 132°−134°; Anal., Calcd. for $C_{24}H_{24}N_2O_2$: Theoretical %: C=77.39; H=6.50; N=7.52 Found %: C=77.24; H=6.68; N=7.67.

e) 2-[1-[2-(4-Chlorobenzyloxyphenoxy)]-2-phenyl]ethylimidazoline m.p. 133°-136°; Anal., Calcd. for $C_{24}H_{23}ClN_2O_2$: Theoretical %: C=70.84; H=5.70; N=6.88 Found %: C=70.68; H=5.80; N=6.85 f) 2-[α-(2-benzyloxyphenoxy)]benzylimidazoline m.p. 126°−129°; Anal., Calcd. for $C_{23}H_{22}N_2O_2$: Theoretical %: C=77.07; H=6.19; N=7.82 Found %: C=76.76; H=6.07; N=7.71.

EXAMPLES OF SYNTHETIC SCHEME I: STEP A

The purpose of this example is to demonstrate the amidation and cyclization reaction which is described in Step A of Reaction Scheme I. Shown in reaction scheme IA is an alkylation reaction between a bromo ester as described by Formula II and an alcohol as described by Formula III.

Ethyl 2-(2-benzyloxyphenoxy)-2-phenylacetate

A mixture of 9.7 g (0.04 M) ethyl α-bromophenylacetate, and 8.0 g (0.04) of 2-benzyloxyphenol, 10 g of potassium carbonate and 120 ml of acetone were refluxed for 24 hours, cooled and filtered. The solvent was removed and the residue was taken up in ethyl acetate. The solution was shaken with dilute sodium hydroxide then saturated sodium chloride. Removal of the solvent and distillation of the residue gave 9.6 g, of product B.p. 170–174/0.04 mm. Characteristics of the isolated compound are as follows: Anal., Calcd. for $C_{23}H_{22}O_4$: C=76.22; H=6.12 Found.: C=76.22; H=6.16

EXAMPLES OF SYNTHETIC SCHEME I: STEP B

The purpose of this example is to demonstrate the amidation and cyclization reaction which is described in Step B of Reaction Scheme I.

1) 2-[1-(2-benzyloxyphenoxy)-2-phenyl]ethylimidazoline (IB:1)

To a solution of 18.1 g (0.049M) of ethyl 2-(2-benzyloxphenoxy)-3-phenylpropionate is 350 ml of dry toluene, 4.65 g (0.077M) of ethylenediamine was added followed by 43 ml of 2M trimethylaluminum in toluene. The mixture was refluxed under nitrogen for 4 hours and cooled in an ice bath. Water (25 ml), followed by 50 ml of methanol, was added and the mixture stirred for 1 hour, filtered and the solvent removed at reduced pressure. Recrystallization from ethyl acetate gave 10.8 g of final product.

melting point 132°–134°. Anal., Calcd. for $C_{24}H_{24}N_2O_2$: C=77.39; H=6.50; N=7.52 Fd: C=77.24; H=6.68; N=7.67

EXAMPLE OF SCHEME II: STEP A

The purpose of this example is to demonstrate a displacement reaction depicted in Step A of Reaction Scheme II.

1) Diethyl 2-benzloxyphenoxymalonate (IIA:1)

A mixture of 20.0 g (0.1M) of 2-benzyloxyphenol, 21.3 g (0.11M) of diethyl chloromalonate, 15 g of potassium carbonate and 200 ml of acetone was refluxed for 16 hours, cooled and filtered. The solvent was removed, the residue, in ether, was washed with water and the organic layer dried over sodium sulfate. Removal of the solvent and distillation of the residue 172°–180°/0.4 mm gave 34.3 g of product.

Anal., Calcd. for $C_{20}H_{22}O_6$: C=67.02; H=6.19 Fd: C=66.58; H=6.46.

Similarly prepared was:

Diethyl 2-(2-phenylethoxy)phenoxymalonate B.p. 162°–167°/0.2 mm Anal., Calcd. for $C_{21}H_{24}O_6$: C=67.73; H=6.50 Fd: C=67.50; H=6.24

EXAMPLE OF SYNTHETIC SCHEME II: STEP B

This example demonstrates the displacement reaction of Step B in Reaction Scheme II.

1) Diethyl benzyl-(2-benzyloxyphenoxy)malonate

To an ice-cooled suspension of sodium hydride (from 2.2 g of a 60% mixture with oil) in 100 ml of dimethylformamide a solution of 17.9 g (0.05M) of diethyl 2-(2-benzyloxy)phenoxymalonate in 25 ml of dimethylformamide was added dropwise. After stirring 20 minutes at room temperature, a solution of 7.0 g (0.055M) of benzyl chloride in 10 ml of dimethylformamide was added all at once and the mixture was heated in an oil bath of 55°–60° for 2 hours. The mixture was cooled in ice and excess sodium hydride was decomposed with acetic acid. The reaction mixture was diluted with water and extracted with carbon tetrachloride. The carbon tetrachloride was removed and the residue shaken with a mixture of acetonitrile and pentane. Concentration of the acetonitrile layer and distillation at 190°–210°/0.2 mm gave the crude ester. Removal of lower boiling material by redistillation left 11.7 g of ester.

Anal., Calcd. for $C_{27}H_{28}O_6$: C=72.30; H=6.29 Fd: C=72.01; H-6.33.

Similarly prepared were:

Diethyl benzyl[2-(2-phenylethoxy)phenoxy]malonate B.p. 205°–210°/0.2 mm Anal. Calcd. for $C_{28}H_{30}O_6$: C=72.71; H=6.54 Fd: C=72.76; H=6.41.

Diethyl 2-benzyloxyphenoxy-4-phenylpropylmalonate B.p. 195°–200°/0.2 mm Anal. Calcd. for $C_{29}H_{32}O_6$: C=73.09; H=6.77 Fd: C=73.16; H=6.77.

Also can be prepared:

Diethyl 2-benzyloxyphenoxy-2-(4-methoxyphenyl)ethylmalonate

Diethyl 2-benzyloxy-4-chlorophenoxy-4-methoxybenzylmalonate

Diethyl 2-(4-chlorobenzyloxy)phenoxy-3-phenylpropylmalonate

EXAMPLES OF SYNTHETIC SCHEME II: STEP C

This example demonstrates the decarbethoxylation reaction of Step C in Reaction Scheme II.

1) Ethyl 2-(2-benzyloxy)phenoxy)-3-phenylpropionate

A mixture of 34.0 g of diethyl benzyl-(2-benzyloxyphenoxy)malonate, 2.78 g of water, 4.45 g of sodium chloride and 240 ml of dimethylsulfoxide was refluxed under nitrogen for 1.5 hours, cooled and diluted with water. The product was extracted into carbon tetrachloride, the extracts dried with magnesium sulfate and the solvent removed. Distillation of the residual oil gave 14.8 g, boiling point 162°–72°/0.3 mm. Anal. C., Calcd. for $C_{24}H_{24}O_3$: C=76.57; H=6.43 Fd: C=75.81; H=6.41

Also prepared:

Ethyl 2-(2-[2-phenylethoxy]phenoxy)-3-phenylpropionate

B.p. 186°–195°/0.3 mm. Anal. Calcd. for $C_{25}H_{26}O_4$: C=76.90; H=6.71 Fd: C=77.00; H=6.61

Ethyl 2-(2-benzyloxyphenoxy)-5-phenylvalerate B.P. 186–90/0.3 mm Anal. Calcd. for $C_{26}H_{28}O_4$: C=77.20; H=6.98 Fd: C=77.11; H=6.99

Also can be prepared:

Ethyl 2-[2-(4-chlorobenzyloxy)phenoxy]-4-(3-methoxyphenyl)butyrate

Ethyl 2-[2-(1-phenylethoxy)phenoxy]-3-(3,4-dichlorophenyl)propionate

Ethyl 2-[2-(2-benzyloxy-4-chloro)phenoxy)-3-(4-methoxyphenyl)propionate

EXAMPLES OF SYNTHETIC SCHEME III

The purpose of this example is to demonstrate the reactions which are described in SCHEME III, Steps A and B.

EXAMPLES OF SYNTHETIC SCHEME III:STEP A 1) 2-[1-(2-hydroxyphenoxy)-2-phenyl]ethylimidazoline hydrochloride (IIIA:1)

A solution of 8.3 g of 2-[1-(2-benzyloxyphenoxy)-2-phenyl]ethylimidazoline in 200 ml of ethanol containing 10 ml of acetic acid was shaken for 8 hours on a Parr hydrogenation apparatus. Concentrated hydrochloric acid (2 ml) was added after filtration of the catalyst. Evaporation of the solvent left an oil which dissolved in acetone. On standing, precipitation occurred to give 5.85 g of salt. Recrystallization from methanol/acetonitrile gave the pure salt, melting point 178°–179°. Anal., Calcd. for $C_{17}H_{18}N_2O_2 \cdot HCl$: C=64.04; H=6.01; N=8.79 Fd: C=64.05; H=6.30; N=8.72

EXAMPLES OF SYNTHETIC SCHEME III:STEP B 1) 2-[1-(2-[4-chlorobenzyloxy)phenoxy)-2-phenyl]ethylimidazoline (IIIB:1)

The hydrochloride salt of 2-[1-(2-hydroxyphenoxy)-2-phenyl]ethylimidazoline (1.3 g, 0.004M) was added to 50 ml of methanol containing 2 equivalents of sodium methoxide. After stirring several minutes, 4-chlorobenzyl chloride (1.1 equivalents) was added and the mixture refluxed for 2.5 hours. After filtration the solvent was removed and the product (0.7 g) isolated by chromatography on silica and elution with hexane-ethyl acetate-diethylamine (100:95:5). Recrystallization from ethyl acetate/hexane gave 0.5 g, melting point 133°–136°. Anal., Calcd. for $C_{24}H_{23}ClN_2O_2$: C=70.84; H=5.70; N=6.88 Fd: C=70.68; H=5.80; N=6.85

EXAMPLES OF SYNTHETIC SCHEME IV:STEP A (1-[2-(4-aminobenzyloxy)phenoxy]-2-phenyl)ethylimidazoline (IV:A)

The (1-[2-(4-nitrobenzyloxy)phenoxy]-2-phenyl)ethylimidazoline can be reduced to a corresponding (1-[2-(4-aminobenzyloxy)phenoxy]-2-phenyl)ethylimidazoline by dissolving the starting compound in ethanol together with excess stannous chloride. The mixture is heated to 50°–60° C. followed by the portionwise addition of sodium borohydride and allowed to further react. After the reaction is complete the final compound is isolated by conventional techniques.

EXAMPLES OF SYNTHETIC SCHEME IV:STEP B (1-[2-(4-acetylaminobenzyloxy)phenoxy]-2-phenyl)ethylimidazoline (IV:B)

The (1-[2-(4-aminobenzyloxy)-phenoxy]-2-phenyl)ethylimidazoline can be alkylated by dissolving the compound in solution of methanol with one or more equivalents of acetylaldehyde in the presence of sodium borohydride or sodium cyanobororhydride. When one equivalent of aldehyde is used the major product is the monoalkylated amine (—NH—R) while with 2 or more equivalents of aldehyde the dialkylated amine (—N(CH$_2$R)$_2$) is the major product isolated by conventional techniques. Similarly, the aldehyde chosen, such as formaldehyde, acetaldehyde, propionaldehyde or the like, is chosen to vary the R group substituted.

EXAMPLES OF RECEPTOR AFFINITY

The purpose of these examples are to demonstrate and exemplify the means by which receptor affinity can be determined.

AFFINITY FOR 5HT$_{1c}$ RECEPTORS

Affinity for 5-HT$_{1c}$ receptors on transfected fibroblast cell membranes by use of the partial agonist 2-[$^{125}$I]iodolysergic acid diethylamide.[Elliott, M. J., Kent, J. Neurochem. 53:191–196, 1989; Peroutka, S. J., Snyder, S. H., Molec. Pharmacol. 16:687–699, 1979; Kadan, J. M., Krohn, A. M., Evans, M. J., Ualtz, R. L., Hartig, P. R., J. Neurochem. 43:601–606, 1984.] One test used to determine the potency of compounds is to test their ability to compete with [$^{125}$I]LSD binding to a NIH 3T3 cell line containing the cloned rat 5-HT$_{1c}$ receptor designated "Po" by its originators.[Julius, D., Livelli, T. J., Jessell, T. M. and Axel, R., Science 244:1057–1062, 1989]

Confluent P$_o$ cell monolayers are dissociated in Versene and centrifuged at 1000 rpm for 5 minutes. The resulting pellet is homogenized in 10 volumes 0.32 M sucrose using a Dounce glass homogenizer, 10 strokes. The suspension is centrifuged at 44,000×g for 15 minutes, and the pellet suspended in 5 volumes 10 mM Hepes-KOH, pH 7.4, using a Polytron. The membranes are then stored at −80° C.

The assay tubes, in triplicate, receive 20 μl of 5 nM 125I]LSD, 20 μl of test Compound (10$^{-9}$M to 10$^{-5}$M or 10 μM mesulergine for nonspecific binding), 40 μl of membrane suspension (1–5 μg protein/assay tube) in a final volume of 0.1 ml of 50 mM Tris-HCl, pH 7.6. Incubations are carried out at 37° C. for 60 minutes and terminated by addition of 2 ml ice-cold assay buffer and filtered through GF/B glass fiber filters (presoaked in 0.1% polyethyleneimine). Filters are washed twice With 5 ml of cold buffer and transferred to polystyrene tubes for radioactivity determination. Protein concentration was measured using the Bradford dye binding method.

Inhibition of [$^{125}$I]LSD binding of 15% or more by a test compound is indicative of affinity for the 5HT1C receptor site. The molar concentration of a compound which causes 50% inhibition of the binding of ligand is the IC$_{50}$. The IC$_{50}$ value is converted to the Ki value by the method of Cheng and Prusoff. [Cheng, Y. -C. and Prusoff, U. H., Biochem. Pharmacol. 22:3099–3108, 1973]. Compounds tested using this assay were observed to have the following affinities listed in the following table.

| Compound No. | COMPOUNDS HAVING AFFINITY FOR THE 5HT$_2$ RECEPTOR Compound Name | AFFINITY FOR 5HT$_{1C}$ RECEPTORS (IC50) |
|---|---|---|
| 101,623 | 2-[1-(2-phenylethoxy phenoxy)-2-phenyl]ethylimidazoline | 14 nM |
| 102,588 | 2-[1-(2-benzyloxy phenoxy)-4-phenyl]butylimidazoline | 82 nM |
| 100,499 | 2-[1-(2-benzyloxy phenoxy)-2-(4-methoxyphenyl)]ethylimidazoline | 2.3 nM |
| 101,600 | 2-[1-(2-benzyloxy phenoxy)-2-phenyl)ethyl imidazoline | 4 nM |

AFFINITY FOR α2-ADRENERGIC RECEPTORS

Affinity for Brain [$^3$H] Rauwolscine Binding Sites (α2-adrenergic receptor) can be determined by the potency of test compounds to compete with the ligand [3H]rauwolscine (RAUW) for the α2-adrenergic receptors prepared from animal brain membranes.

Young adult male rats (C-D strain), obtained from Charles River, are killed by decapitation and the brains are immediately removed. Receptors are prepared from rat cerebral cortices.[Cheung Y, Barnett DB and Nahorski SR,. Eur. J. Pharmacol. 84:79–85, 1982] The tissue is homogenized in 20 vol ice-cold 5 mM Tris HCl, 5 mM EDTA, pH 7.5, using a Polytron (setting 7 for 10 seconds). The homogenate is centrifuged at 15,000 rpm for 10 minutes at 4° C. The resulting pellet is resuspended in 20 vol with the same buffer using a Dounce homogenizer and centrifuged as before. One final washing is carried out by resuspending the pellet in ice-cold assay buffer (50 mM Tris-HCl, 0.5 mM EDTA, 0.1% ascorbic acid, pH 7.5) and centrifuged as before. The pellet is finally resuspended in 15 ml of the assay buffer per gram of original wet weight of tissue.

The incubation tubes, in triplicate, receive 100 μl of [$^3$H]-RAUW, 1.0 nM in the assay, 100 μl of test compounds at various concentrations over the range of 10$^{-10}$M to 10$^{-5}$M diluted with assay buffer, 0.2 ml of membrane suspension (13 mg wet weight), in a final volume of 1 ml with assay buffer (50 mM Tris-HCl, 0.5 mM EDTA, 0.1% ascorbic acid, pH 7.5). Incubations are carried out at 25° C. for 60 minutes. Each tube is terminated within 1.0 seconds by filtration through GF/B glass fiber filters using a vacuum. The filters are rinsed two times with 5 ml of ice-cold assay buffer. The membranes on the filters are transferred to scintillation vials to which 8 ml of Omnifluor with 5% Protosol is added. The filters are counted by liquid scintillation spectrometry.

Specific binding of [³H]RAUW is measured as the excess over blanks taken in the presence of 10 μM yohimbine. Total membrane-bound radioactivity is about 3% of that added to the test tubes. Since these conditions limit total binding to less than 10% of the radioactivity, the concentration of free ligand does not change appreciably during the binding assay. Specific binding to membranes is about 70% of the total bound. Protein content of the membrane suspension is determined by the method of Lowry. et al.[Lowry DH, Rosebrough NJ, Farr AL and Randall RJ. , J. Biol. Chem. 193: 265–275, 1951].

Inhibition of [³H]RAUW binding of 15% or more by a test compound is indicative of affinity for the α2-adrenergic site. The molar concentrateion of compound which causes 50% inhibition of the binding of ligand is the IC50. A value in the range of 1–10 nM would indicate a highly potent compound

AFFINITY FOR 5-HT2 RECEPTORS

Affinity for 5-HT$_2$ receptor on transfected fibroblast cell membranes (partial agonist [¹²⁵I]lysergic acid diethylamide; Elliott, M. J., Kent, A., J. Neurochem. 53: 191–196, 1989.; Peroutka, S. J., Snyder, S. H. , Molec. Pharmacol. 16: 687–699, 1979; Kadan, J. M., Krohn, A. M., Evans, M. J., Ualtz, R. L., Hartig, P. R.; J. Neurochem. 43: 601–606, 1984) is used to determine the potency of test compounds to compete with [¹²⁵I]LSD binding to a NIH 3T3 cell line containing the cloned rat 5-HT$_2$ receptor designated "GF-6" by its originators.- [Julius, D., Huang, K. N., Livelli, T. J., Axel, R., and Jessell, T. M., Proc. Natl. Acad. Sci. USA 87:928–932, 1990]

Confluent GF6 cell monolayers are dissociated in Versene and centrifuged at 1000 rpm for 5 minutes. The resulting pellet is homogenized in 10 volumes 0.32M sucrose using a Dounce glass homogenizer, 10 strokes. The suspension is centrifuged at 44,000×g for 15 minutes, and the pellet suspended in 5! volumes 10 mH Hepes-KOH, pH 7.4, using a Polytron. The membranes are then stored at −80° C.

The assay tubes, in triplicate, receive 20 μl of 5 nM [¹²⁵I]LSD, 20 μl of test compound ($10^{-9}$M to $10^{-5}$M or 10 μM ketanserin for nonspecific binding), 40 μl of membrane suspension (1–5 μg protein/assay tube) in a final volume of 0.1 ml of 50 mM Tris- HCl, pH 7.6. Incubations are carried out at 37° C. for 60 minutes and terminated by addition of 2 ml ice-cold assay buffer end filtered through GF/B glass fiber filters (presoaked in 0.1% polyethyleneimine). Filters are washed twice with 5 ml of cold buffer and transferred to polystyrene tubes for radioactivity determination. Protein concentration was measured using the Bradford dye binding method.

Inhibition of [¹²⁵I]LSD binding by a test compound is indicative of affinity for the 5HT$_2$ receptor site. The molar concentration of a Compound which causes 50% inhibition of the binding of ligand is the IC$_{50}$. The IC$_{50}$ value is converted to the Ki value by the method of Cheng and Prusoff.[Cheng, Y. -C and Prusoff, Biochem. Pharmacol. 22:3099–3108, 1973]. Compounds tested using this assay were observed to have the following affinities listed in the table given below.

COMPOUNDS HAVING AFFINITY FOR THE 5HT$_2$ RECEPTOR

| Compound No. | Compound Name | AFFINITY FOR 5HT$_2$ RECEPTORS (IC50) |
|---|---|---|
| 101,623 | 2-[1-(2-phenylethoxy phenoxy)-2-phenyl]ethylimidazoline | 14 nM |
| 102,588 | 2-[1-(2-benzyloxy phenoxy)-4-phenyl]butylimidazoline | 167 nM |
| 100,499 | 2-[1-(2-benzyloxy phenoxy)-2-(4-methoxyphenyl)]ethyl midazoline | 3.5 nM |
| 101,600 | 2-[1-(2-benzyloxy phenoxy)-2-phenyl)ethyl imidazoline | 2.5 nM |

ANTAGONISM OF SEROTONIN (5HT) STIMULATED PHOSPHOINOSITIDE TURNOVER IN BRAIN SLICES OR CULTURED CELLS

Antagonism of Serotonin (5HT) Stimulated Phosphoinositide Turnover in Brain Slices or Cultured Cells (GF6, Po)is used to determine the potency of test compounds to antagonize serotonin stimulated phosphatidylinosotide turnover in brain slices or cultured cells. Berridge, M. J. et al. Biochem. J. 206:587–595, 1982; Kendall, D. A. and Hill, in Methods in Neurotransmitter Receptor Analysis, ed. H. I. Yamamura, S. J. Enna, M. J Kujar, Raven Press 1990, pages 69–87; Sanders-Bush, et al., Annals New York Acad. Sciences 4:236, 1990.

Typically, 3H-myo-inositol (spec. act. 80 Ci/mM) is preincubated with brain slices in Krebs/NaHCO$_3$ (60 uCi/100 mg tissue for 2 Hrs.) or cultured cells (3 uCi/well for 1 or 2 days) in appropriate tissue culture media. The samples are then washed three times with 400 μL of 5 mM unlabeled inositol in Krebs/NaHCO$_3$ and 400 ul Krebs/NaHCO$_3$ added per sample Assay tubes or wells, in triplicate, are preincubated for 10 min. with the test compound prior to the addition of the agonist serotonin. After an appropriate incubation time with the agonist in a final volume of 500ul, the reaction is stopped by the addition of either 4 volumes chloroform/methanol ($\frac{1}{2}$,v/v) for slices or 1 volume 10% perchloric acid for cultured cells. Phosphatidylinosotide metabolites (IP$_{1,2,3}$) are then extracted and quantified by ion exchange chromatography using Bio-Rad AG-1-X8 resin (100–200mesh, formate form. Berridge, M. J. et al. Biochem. J. 206:587–595, 1982; Kendall, D. A. and Hill, in Methods in Neurotransmitter Receptor Analysis, ed. H. I. Yamamura, S. J. Enna, M. J. Kujar, Raven Press 1990, pages 69–87. The metabolites of interest are eluted from the columns with 10 ml 1M ammonium formate/0.1% formic acid and 1 ml is counted by liquid scintillation spectroscopy.

Inhibition of 5HT stimulated PI turnover by a test compound is indicative of a compound with antagonist properties. The molar concentration of a compound which causes 50% inhibition of a maximal 5HT responce is the IC$_{50}$. An IC$_{50}$ value in the range of 1–10 nM would indicate a highly potent compound.

What is claimed is:

1. A compound of the formula 1:

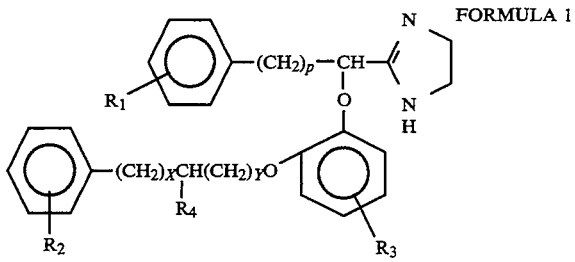

FORMULA 1 wherein:
- R₁ is represented by substituent selected from the group consisting of hydrogen, halogen, $C_{1-4}$ alkyl, $C_{1-4}$ alkoxy, —$NO_2$, and —$NR_5R_6$;
- R₂ is represented by a substituent selected from the group consisting of hydrogen, halogen, $C_{1-4}$ alkyl, $C_{1-4}$ alkoxy, and —$NR_5R_6$;
- R₃ is represented by a substituent selected from the group consisting of hydrogen, halogen, $C_{1-4}$ alkyl, and $C_{1-4}$ alkoxy;
- R₄ is represented by a substituent selected from the group consisting of hydrogen, and halogen;
- R₅ and R₆ is independently selected from the group consisting of hydrogen and $C_{1-4}$ alkyl;
- p is represented by the integer 0, 1, 2, 3, or 4;
- x is represented by an integer from 0-2;
- y is represented by an integer from 0-2;

with the proviso that at least R₁ or R₂ is chosen as $NO_2$ or —$NR_5R_6$;
or the compounds of formula 1 may be a pharmaceutically acceptable salt thereof.

2. A pharmaceutically acceptable acid addition salt of claim 1.

3. A pharmaceutical composition comprising an effective amount of a compound of claim 1 in admixture with an inert carrier.

4. A compound according to claim 1 wherein p is 1–3.

5. A compound according to claim 1 wherein R₁ is amino.

6. A compound according to claim 1 wherein R₁ is nitro.

7. A compound according to claim 1 wherein R₂ is amino.

8. A compound according to claim 1 wherein R₂ is nitro.

9. A compound as in claims 5, 6, 7, or 8 wherein R₄ is nitro.

10. A compound as in claims 5, 6, 7, or 8 wherein R₃ is hydrogen.

11. A compound according to claim 1 having the structure of 2-(1-[2-(4-aminobenzyloxy)phenoxy]-2-phenyl)ethylimidazoline.

12. A compound according to claim 1 having the structure of 2-(1-[2-(4-nitrobenzyloxy)phenoxy]-2-phenyl)ethylimidazoline.

13. A compound according to claim 1 having the structure of 2-(1-[2-(4-aminobenzyloxy)phenoxy]-2-phenyl)propylimidazoline.

14. A compound according to claim 1 having the structure of 2-(1-[2-(4-nitrobenzyloxy)phenoxy]-2-phenyl)propylimidazoline.

15. A compound according to claim 1 having the structure of 2-(1-[2-(4-aminobenzyloxy)phenoxy]-2-phenyl)butylimidazoline.

16. A compound according to claim 1 having the structure of 2-(1-[2-(4-nitrobenzyloxy)phenoxy]-2-phenyl)butylimidazoline.

17. A compound according to claim 1 having the structure of 2-[1-(2-benzyloxyphenoxy)-2-(4-nitrophenyl)ethylimidazoline.

18. A compound according to claim 1 having the structure of 2-[1-(2-benzyloxyphenoxy)-2-(4-aminophenyl)ethylimidazoline.

19. A compound according to claim 1 having the structure of 2-[1-(2-benzyloxyphenoxy)-2-(4-nitrophenyl)propylimidazoline.

20. A compound according to claim 1 having the structure, of 2-[1-(2-benzyloxyphenoxy)-2-(4-aminophenyl)propylimidazoline.

21. A compound according to claim 1 having the structure of 2-[1-(2-benzyloxyphenoxy)-2-(4-nitrophenyl)butylimidazoline.

22. A compound according to claim 1 having the structure of 2-[1-(2-benzyloxyphenoxy)-2-(4-aminophenyl)butylimidazoline.

23. A method of using a compound according to claim 1 as a $5HT_{1C}$ antagonist for the treatment of depression comprising administering an effective amount of said compound to a patient in need thereof.

24. A method of using a compound according to claim 1 as a $5HT_{1C}$ antagonist for the treatment of anxiety comprising administering an effective amount of said compound to a patient in need thereof.

25. A method of using a compound according to claim 1 as a $5HT_{1C}$ antagonist for the treatment of a migraine comprising administering in effective amount of said compound to a patient in heed thereof.

26. A method of using a compound according to claim 1 for the treatment of hypertension comprising administering an effective amount of said compound according to a patient in need thereof.

* * * * *

UNITED STATES PATENT AND TRADEMARK OFFICE
CERTIFICATE OF CORRECTION

PATENT NO. : 5,407,954
DATED : April 18, 1995
INVENTOR(S) : Jules Freedman, et al.

It is certified that error appears in the above-indentified patent and that said Letters Patent is hereby corrected as shown below:

Column 1, line 50, the patent reads "selected from hydrogen", and should read --selected from the group consisting of hydrogen --.
Column 3 line 23, the patent reads "bonded!", and should read --bonded--.
Column 9, line 55, the patent reads "Of", and should read --of --.
Column 10, line 61, the patent reads "Which", and should read --which --.
Column 14, line 16, the patent reads " from 1 t o 4", and should read --from 1 to 4 --.
Column 15, line 48, the patent reads "or,gelatin,", and should read --or gelatin --.
Column 18, line 11, the patent reads "Was", and should read --was --.
Column 19, line 63, the patent reads "Compound", and should read --compound --.
Column 21, line 19, the patent reads "concentrateion", and should read --concentration --.
Column 21, line 44, the patent reads "5!", and should read --5 --.
Column 21, line 54, the patent reads "buffer end", and should read --buffer and --.
Column 21, line 61, the patent reads "Compound", and should read --compound --.
Column 22, line 32, the patent reads "4:236, 1990", and should read --224:236, 1990 --.
Column 22, line 41, the patent reads "sample Assay", and should read --sample assay --.
Column 23, line 50, the patent reads "$R_4$ is nitro", and should read --$R_3$ is hydrogen --.
Column 23, line 52, the patent reads "$R_3$ is hydrogen", and should read --$R_4$ is hydrogen --.
Column 24, line 48, the patent reads "in heed thereof", and should read --in need thereof--.

Signed and Sealed this

Third Day of June, 1997

BRUCE LEHMAN

Attest:

Attesting Officer

Commissioner of Patents and Trademarks